US008999268B2

(12) United States Patent
Egger-Cimenti et al.

(10) Patent No.: US 8,999,268 B2
(45) Date of Patent: Apr. 7, 2015

(54) SAMPLE INPUT DEVICE FOR INPUTTING LIQUID SAMPLES

(75) Inventors: Felix Egger-Cimenti, Graz (AT); Stefan Gulo, Riederhof (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 375 days.

(21) Appl. No.: 13/409,282

(22) Filed: Mar. 1, 2012

(65) Prior Publication Data

US 2012/0160331 A1 Jun. 28, 2012

Related U.S. Application Data

(63) Continuation of application No. PCT/EP2010/063578, filed on Sep. 15, 2010.

(30) Foreign Application Priority Data

Sep. 17, 2009 (AT) ................. A 1474/2009

(51) Int. Cl.
*G01N 35/10* (2006.01)
*B01L 3/00* (2006.01)
*G01N 33/49* (2006.01)

(52) U.S. Cl.
CPC ......... *B01L 3/502715* (2013.01); *B01L 3/5635* (2013.01); *B01L 3/502723* (2013.01); *B01L 2200/026* (2013.01); *B01L 2200/027* (2013.01); *B01L 2200/0684* (2013.01); *B01L 2300/0681* (2013.01); *B01L 2300/0838* (2013.01); *G01N 33/49* (2013.01)

(58) Field of Classification Search
CPC .. G01N 35/10; G01N 35/1095; B01L 3/0275; B01L 3/0279

USPC .................. 422/501, 513; 73/864.21
See application file for complete search history.

(56) References Cited

U.S. PATENT DOCUMENTS

| 6,016,712 A  | * | 1/2000  | Warden et al. ............. 73/864.21 |
| 7,837,943 B2 | * | 11/2010 | Jeong et al. .................... 422/501 |
| 7,896,818 B2 | * | 3/2011  | Fremming et al. ............ 600/573 |

(Continued)

FOREIGN PATENT DOCUMENTS

| DE | 19949561 A1 | 4/2000 |
| DE | 202006010970 U1 | 9/2006 |

(Continued)

OTHER PUBLICATIONS

International Search Report issued Mar. 24, 2011 in PCT Application No. PCT/EP2010/063578, EN translation.

(Continued)

*Primary Examiner* — Peter Macchiarolo
*Assistant Examiner* — Nathaniel Kolb
(74) *Attorney, Agent, or Firm* — Roche Diagnostics Operations, Inc.

(57) ABSTRACT

A sample input device for transferring liquid samples, typically blood samples, from sample containers, typically syringes, into analyzer devices for examining the composition of the samples, wherein the sample input device comprises retention elements for at least partly keeping particulate components of the sample from passing over from the sample container into the analyzer, and wherein the sample input device further contains at least one ventilation device that allows ventilating the sample container while transferring the sample from the sample container into the analyzer, typically when aspirating the sample via the analyzer.

24 Claims, 5 Drawing Sheets

(56) References Cited

U.S. PATENT DOCUMENTS

| | | | |
|---|---|---|---|
| 8,444,621 B2* | 5/2013 | Fremming et al. | 604/403 |
| 2003/0236497 A1* | 12/2003 | Fremming et al. | 604/126 |
| 2007/0163366 A1* | 7/2007 | Jeong et al. | 73/864.87 |
| 2007/0282224 A1 | 12/2007 | Gulo | |
| 2011/0144593 A1* | 6/2011 | Fremming et al. | 604/199 |

FOREIGN PATENT DOCUMENTS

| | | | |
|---|---|---|---|
| EP | 0573884 | A2 | 12/1993 |
| EP | 1347282 | A2 | 9/2003 |
| EP | 1909101 | A1 | 4/2008 |
| WO | 85/02830 | A1 | 7/1985 |
| WO | 92/19949 | A1 | 11/1992 |
| WO | 2010/140137 | A3 | 12/2010 |

OTHER PUBLICATIONS

Anonymous, "Mini-Spike Medikamentenzubereitung war nie einfacher . . . " B. Braun Melsungen AG Product Information, Jan. 14, 2009, retrieved from Internet Feb. 25, 2011, 5 pages.

Anonymous, "Protective Admixture Tools," B. Braun Melsungen AG Product Information, Jan. 1, 2011, 16 pages.

* cited by examiner

SAMPLE INPUT DEVICE FOR INPUTTING LIQUID SAMPLES

CROSS-REFERENCE TO RELATED APPLICATIONS

This application is a continuation of International Application No. PCT/EP2010/063578, filed 15 Sep. 2010, which claims the benefit of Austrian Patent Application No. A 1474/2009, filed 17 Sep. 2009, the disclosures of which are hereby incorporated by reference in their entirety.

TECHNICAL FIELD

The present disclosure relates to sample input devices for transferring liquid samples, typically blood samples, from sample containers, typically syringes, into analyzer devices for examining the composition of the samples. In particular, the disclosure relates to sample input devices for transferring medical samples, typically whole blood, serum and plasma, from different sample containers into analyzing devices for analyzing the blood.

BACKGROUND

Examples of such analyzing devices are blood gas analyzers, which are, for example, provided as portable analyzers for determining POC (Point Of Care) parameters, for example blood gases ($O_2$, $CO_2$, pH), electrolytes (e.g., $K^+$, $Na^+$, $Ca^{++}$, $Cl^-$), metabolites (e.g., glucose and lactate), hematocrit, hemoglobin parameters (e.g., tHb, $SO_2$, etc.) and bilirubin, and which are mainly used for decentralized and quick determination of the above parameters in whole blood samples. Examples of such analyzers are the cobas b 123 and cobas b 221 systems from Roche Diagnostics. Analogous uses in veterinary medicine and the use of serum, plasma, urine and dialysate samples are also common.

In some cases, such analyzers are especially made for only one type of sample container, so that the device-side input facility only allows sample input by means of, for example, a syringe or a capillary tube.

Common sample containers that are used for transporting samples from a sample collection site to an analyzer and the device-side sample input facility thereof are, especially for blood samples:

Syringes: Syringes, in particular specifically adapted blood gas analysis syringes, available in the market may be made of plastic or glass, and can differ in their filling volume (approx. 1 ml to 20 ml) and the anticoagulant used. The conical parts of syringes, where the needles are connected for taking blood samples, are standardized by the Luer standard (DIN-EN20594-1; EN1707; EN20594-1). In addition, the minimum inner diameter of a Luer taper is defined by the standard for sterile hypodermic syringes for single use (EN ISO 7886-1). Due to the large filling volume, one syringe often provides enough sample for several measurements.

Capillary tubes: Capillary tubes, especially those for blood gas analyses, available in the market may be made of plastic or glass, and again can differ in their filling volume and the anticoagulant used. However, the filling volume of capillary tubes is significantly less than that of syringes (approx. 50 μL to 250 μL) and thus provides for only one analysis per sample container. Furthermore, the outside diameter of capillary tubes that may be used depends on the filling volume and the analyzer employed.

In conventional analyzing devices, the device-side sample input may be divided into two main groups:

Filling mouth: A filling mouth is usually made of a soft plastic material, where, depending on the analyzer used, capillary tubes and/or syringes may be connected. Depending on the analyzer and mode of operation used, different input methods are possible:

Aspiration: is possible from capillary tubes (e.g., with the cobas b 123 from Roche Diagnostics). The capillary tube is attached to the filling mouth. Then, the sample is automatically aspirated by the analyzer.

Injection: is possible with syringes (e.g., with the cobas b 221 from Roche Diagnostics). The syringe is pressed against the filling mouth. Then, the sample is actively injected by the user.

Aspiration needle: Some blood gas analyzers, such as the cobas b 221 and the cobas b 123, are equipped with a retractable needle (steel tube) alone or in combination with a filling mouth. The tube is inserted into an opening of the sample container, for example a syringe. Depending on the analyzer used, insertion of the tube is either executed manually or automatically by the analyzer. Then, the analyzer aspirates the sample via the tube.

The following table provides an overview of the sample input examples by means of selected blood gas analyzers. In the table, "Yes" means that the sample input type stated is possible with the respective analyzer.

TABLE 1

Examples of sample input by means of selected blood gas analyzers

| | Filling mouth | | | |
| --- | --- | --- | --- | --- |
| Analyzer | Aspiration from capillary tube | Aspiration from syringe | Injection with syringe | Aspiration tube for syringe |
| cobas b 121/OMNI C | Yes | No* | No | Yes |
| cobas b 221/OMNI S | Yes | No* | Yes | Yes |
| cobas b 123 | Yes | No* | No | Yes |
| OPTI ® CCA | Yes | No* | No | No |

*Note:
Yes, with additional adaptor - for OPTI ® CCA, such an adaptor is available.

Coagulate traps or "clot catchers" can be used to prevent blood clots and tissue particles from entering the analyzer. Clot catchers help prevent blockages in the device or false measurement results due to blood clots by means of integrated retention elements, for example an integrated mechanical grid. Alternatively, appropriate filter or sieve structures as well as other retention elements known to the skilled person may be used as retention devices.

Such a clot catcher may, for example, be used in an analyzer that is equipped with a filling mouth and operated in the aspiration mode using capillary tubes as sample containers, wherein the clot catcher is placed between the capillary tube and the filling mouth.

In other embodiments, a clot catcher may, for example, be used in an analyzer that is equipped with a filling mouth and operated in the injection mode using syringes as sample containers, wherein the clot catcher is placed between the syringe and the filling mouth.

In analyzers equipped with sample input devices working via aspiration needles, usually no clot catcher is used.

The clot catcher available from Roche Diagnostics is, without limitation, suitable for all measurements with capillary tubes and Roche Microsampler® containers. However, in combination with syringes, the clot catcher is typically only suitable for devices and operation modes where the user can actively inject the sample. This clot catcher is made of a thermoplastic elastomer (TPE).

When using this known clot catcher, it is firmly slid onto the sample container filled with blood (e.g., a capillary tube, a Roche Microsampler® container, or a syringe). Then, an analysis is conducted according to the respective instruction manuals.

A disadvantage of all clot catchers known from the state of the art is that with analyzers, the design or the mode of operation of which allows aspiration of a sample only up to a certain point; they do not allow the use of syringes as sample containers.

SUMMARY

It is against the above background that the embodiments of the present disclosure provide certain unobvious advantages and advancements over the prior art. In particular, the inventors have recognized a need for improvements in sample input devices for inputting liquid samples.

Although the embodiments of the present disclosure are not limited to specific advantages or functionality, it is noted that the present disclosure provides a sample input device that allows the use of syringes as sample containers in combination with clot catchers also in analyzers, where no active injection, but only aspiration of the sample by the device is possible, or which are operated in the aspiration mode.

According to one embodiment, a sample input device for transferring liquid samples, typically blood samples, from sample containers, typically syringes, into analyzers for examining the composition of the respective sample is provided, wherein the sample input device comprises: at least one retention element for at least partly keeping particulate components of the sample from passing over from the sample container into the analyzer, and wherein the sample input device further comprises at least one ventilation device that allows ventilating the sample container while transferring the sample from the sample container into the analyzer, typically when aspirating the sample via the analyzer.

According to another embodiment, a method for transferring liquid samples from a sample container into an analyzer for examining the composition of the samples is provided, comprising: providing a sample input device according to an embodiment of the present disclosure; connecting the sample input device to a sample exit of the sample container; connecting the sample input device to a sample entrance of the analyzer; and aspirating the liquid sample from the sample container into the analyzer by subpressure created in the analyzer.

These and other features and advantages of the embodiments of the present disclosure will be more fully understood from the following detailed description taken together with the accompanying claims. It is noted that the scope of the claims is defined by the recitations therein and not by specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

LIST OF REFERENCE NUMBERS

Figure 1:
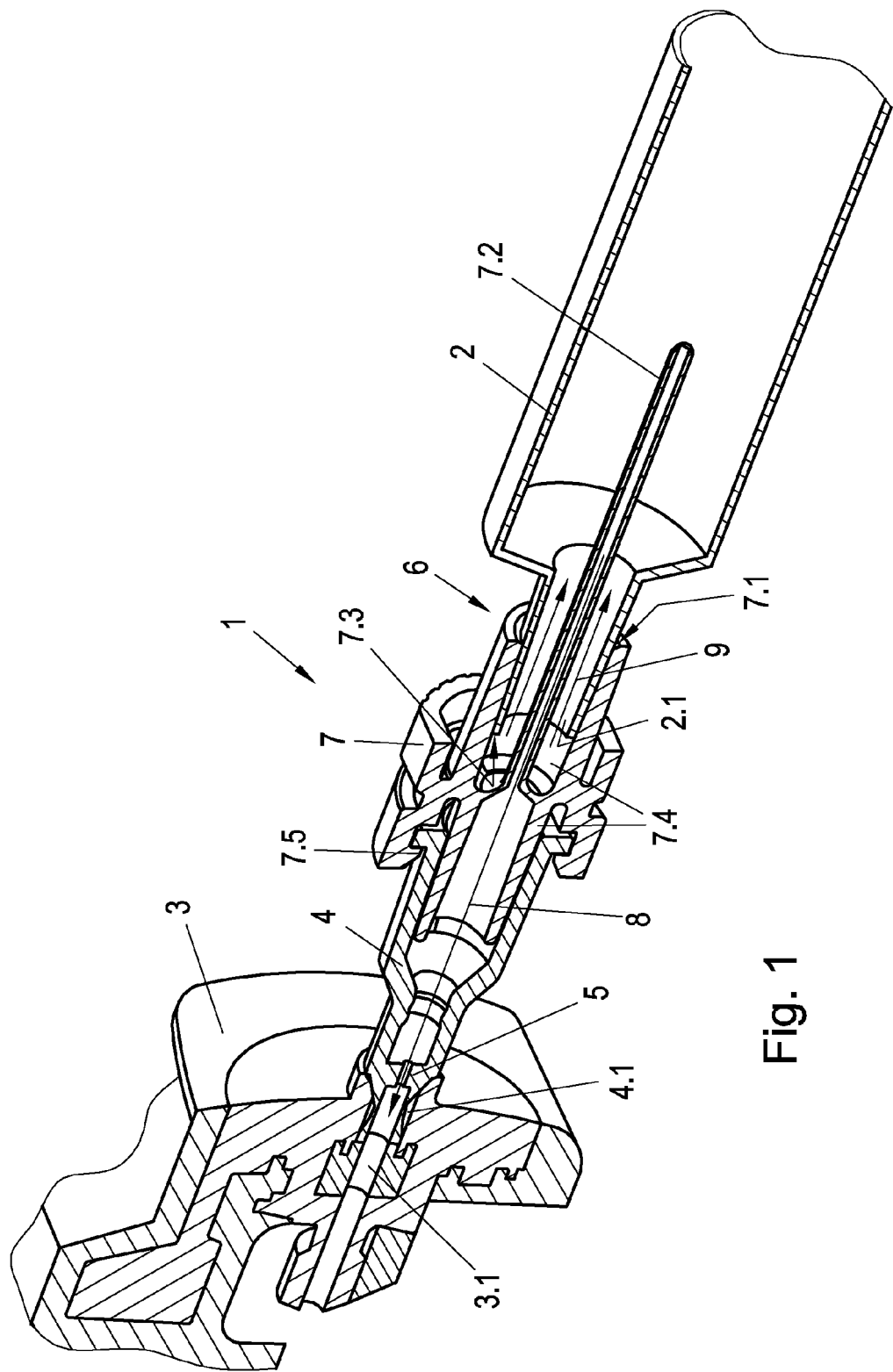
FIG. 1 is a longitudinal section of an oblique view of an embodiment of a multi-component sample input device with a sample container attached thereto, attached to the sample entrance of an analyzer.

1 Sample input device; or variation 1.A
2 Sample container (syringe)
2.1 Sample exit
3 Analyzer
3.1 Sample entrance
4 Analyzer connecting part (clot catcher)
4.1 Attachment area to analyzer
5 Retention element
6 Ventilation device
7 Sample container connecting part (ventilation adaptor); or variations 7.A; 7.B
7.1 Ventilation channel
7.2 Aspiration tube
7.3 Sample container attachment device
7.4 Luer taper connection
7.5 Snap hook
7.6 Circumferential ring
8 Sample path (direction of the arrow)
9 Air path (direction of the arrow)

Skilled artisans appreciate that elements in the figures are illustrated for simplicity and clarity and have not necessarily been drawn to scale. For example, the dimensions of some of the elements in the figures may be exagerated relative to other elements to help improve understanding of the embodiment(s) of the present invention.

DETAILED DESCRIPTION

In accordance with one embodiment of the disclosure, an analyzer connecting device is provided in the form of a functional sample input device unit by combining a clot catcher known from the state of the art, for example a clot catcher from Roche Diagnostics, with a ventilation device for ventilating the sample container.

Known ventilation devices are, for example, ventilation adaptors or attachable parts for syringes allowing air exchange while the analyzer aspirates the sample. Such ventilation adaptors are, for example, sold by OPTI Medical Systems together with the sensor cassette for the OPTI® CCA system. Here, the ventilation adaptor is attached to a syringe filled with sample material.

Subsequently, the front part of the ventilation adaptor is attached to the filling mouth of the analyzer device, and the sample is aspirated by the device. While the sample is aspirated into the analyzer, sample material aspirated from the syringe is replaced by air that enters the syringe via the ventilation adaptor.

With regard to the sample input device, it is useful that the at least one retention device is provided as a mechanical retention device, in particular as a grid, filter or sieve.

Within the framework of the present disclosure it is also possible to provide several retention elements in the same section of the sample input device or in different sections that are spaced apart.

Typically, the ventilation device of the sample input device is provided as a ventilation channel.

Sample input devices with several ventilation devices are also contemplated, in accordance with the present disclosure. In addition, a person skilled in the art knows alternative ventilation or aeration devices that can be used analogously according to one or more embodiments disclosed. Examples of further possible ventilation devices are gas-permeable, but liquid-impermeable membranes or filters, or appropriate deaeration valves that allow air to enter.

In one possible embodiment, a common clot catcher used as retention element is connected with a ventilation adaptor arranged between the syringe and the clot catcher and allowing ventilation of the syringe during aspiration. The two components may be joined firmly or loosely and thus form a corresponding inventive functional unit of a sample input device.

A sample input device comprising an aspiration tube insertable into the sample container, for example a syringe, is further contemplated.

In another embodiment of the disclosure, at least one retention element is provided in the aspiration tube.

In this typical embodiment it is thus also possible to provide the complete sample input device, which comprises at least one retention element as well as at least one ventilation device, as a single piece. One advantage of such a single-piece sample input device is that it is not necessary to have several individual parts on stock and to assemble them.

Similarly, a sample input device consisting of individual components also allows the integration of at least one retention element in the aspiration tube, as well as for example of further retention elements in the analyzer connecting part, the clot catcher.

An exemplary ventilation adaptor effects on the one hand ventilation of the syringe during aspiration of the sample from the syringe, and on the other hand allows, in accordance with further embodiments of the disclosure, further functions, either separately or in combination.

In accordance with yet another typical embodiment of the disclosure, the retention elements and the ventilation devices of the sample input device are implemented in individual components that are assembled in a tight manner to provide a functional unit, especially by connecting the individual components by means of a Luer taper connection.

Here, the front part of the ventilation adaptor is formed according to the Luer standard in order to allow the clot catcher to be fitted directly to the ventilation adaptor. Thus, a releasable connection is achieved between the individual components, the analyzer connecting part (clot catcher) and the sample container connecting part (ventilation adaptor). The analyzer connecting part, i.e., the component comprising for example retention elements, is fixed to the sample container connecting part by mounting it to the Luer taper of the ventilation adaptor.

Alternatively, embodiments are possible wherein the two individual components—the analyzer connecting part (clot catcher) and the sample container connecting part (ventilation adaptor)—may, for example, be fixed by means of two snap hooks. In this way, the two individual components are connected unreleasably.

Sample input devices are useful wherein the individual components comprise an analyzer connecting part connectable to the sample entrance of the analyzer, the retention elements being arranged in the analyzer connecting part.

A sample input device is provided in accordance with yet another embodiment of the disclosure comprising individual components, wherein a sample container connecting part is provided that is connectable to a sample exit of the sample container, the ventilation devices being arranged in the sample container connecting device.

To improve the haptic features and to allow use with Luer lock syringes, in accordance with yet another embodiment, the sample input device is provided with an additional circumferential ring, for example at the sample container connecting part.

The analyzer connecting part is typically made of a styrene-ethylene-butylene-styrene material.

For example, methyl-methacrylate-acrylonitrile-butadien-styrene (MABS), copolyesters, or polyethylene terephthalate have been shown to be useful materials for manufacturing sample container connecting parts. Due to its rigidity, styrene acrylonitrile (SAN) is also suitable for manufacturing sample container connecting parts.

In a further typical embodiment of the disclosure, the sample input device comprises a sample container attachment device, especially a Luer taper connection, which forms a releasable connection with the sample container.

Ventilation devices can also be provided as ventilation slits or ventilation channels in the sample container attachment device.

FIG. 1 shows a first embodiment of a multi-component sample input device 1. The sample input device 1 is provided with ports for connecting to a sample container 2, for example a syringe filled with sample material, and an analyzer 3. The sample input device 1 shown consists of several components and comprises an analyzer connecting part 4 having a retention element 5 in the interior. The analyzer connecting part 4 is further provided with an attachment area 4.1 to the analyzer 3.

Here, the retention element 5 is for example a mechanical grid that at least partly keeps particulate components of the sample from passing over from the sample container 2 into the analyzer 3.

If the liquid sample to be analyzed that is contained in the sample container 2 is, for example, a blood sample, the retaining element 5 keeps back blood clots and thus helps prevent blockages that can cause false measurement results in the analyzer device 3.

Furthermore, the sample input device 1 is provided with ventilation devices 6. For this purpose, for example, several ventilation channels 7.1 for ventilating the sample container 2 during input of the sample into the analyzer 3 are provided in the sample container connecting device 7, to which a sample container 2 is connectable, for example by sliding it on. While the sample material is carried from the interior of the sample container 2 in the direction of arrow 8 through the sample input device 1 to the sample entrance 3.1 of the analyzer 3, air enters into the interior of the sample container 2 in the direction of arrow 9 through the ventilation devices 6, i.e., the ventilation channels 7.1 provided.

The sample container connecting part 7 has an aspiration tube 7.2 that protrudes into the interior of the connected sample container 2, for example of a syringe. Furthermore, the sample container connecting part 7 is provided with a sample container attachment device 7.3, which, in this case, is provided as a Luer taper 7.4 and with which the sample container 2, which is provided with a complementary Luer taper 7.4 in the area of the sample exit opening 2.1 thereof, forms a releasable Luer taper connection.

The individual components of the sample input device 1, the analyzer connecting part 4, and the sample container connecting part 7 are unreleasably connected to each other by means of a snap hook connection 7.5.

Figure 2:
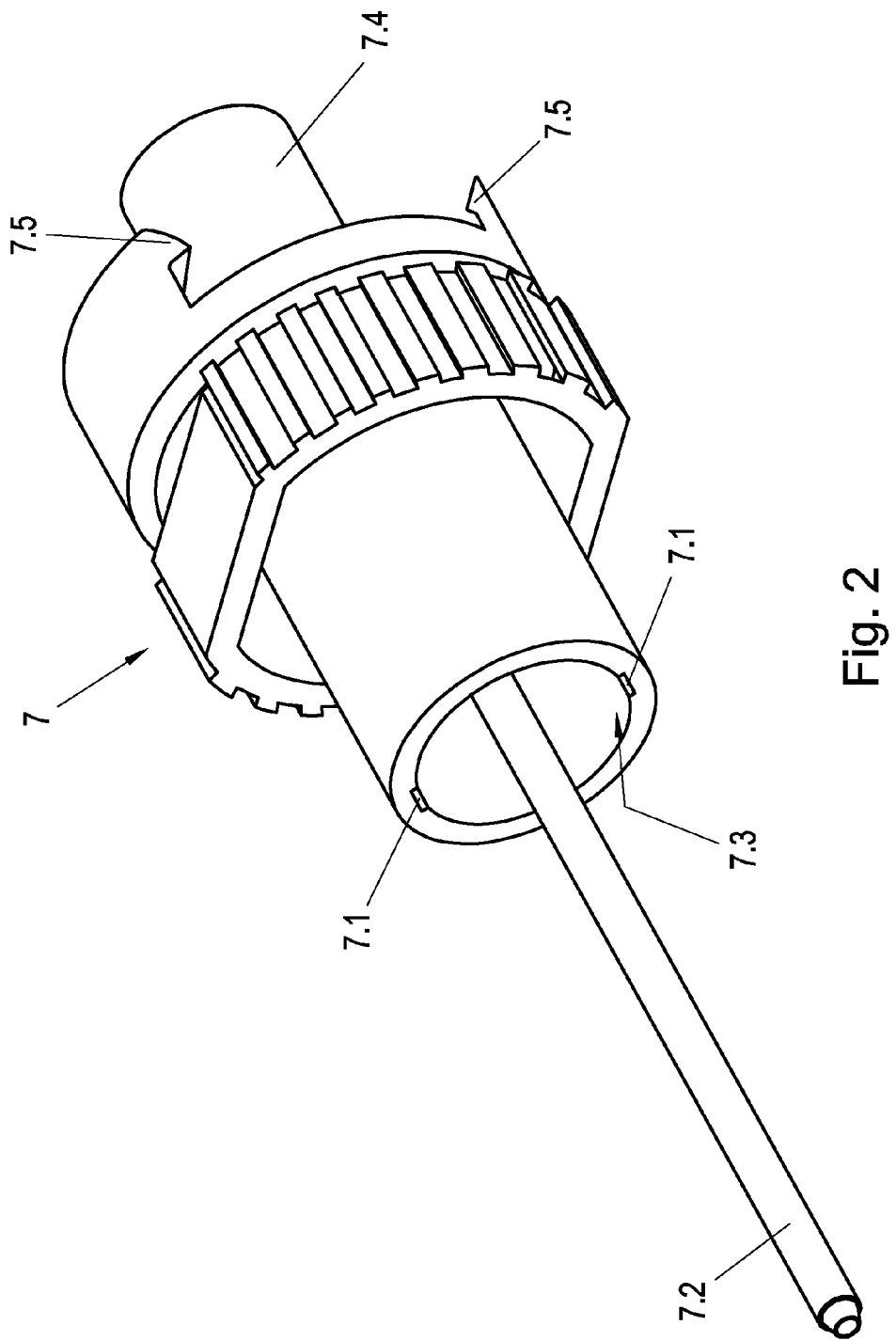
FIG. 2 is a detailed oblique side view of a sample container connecting part.

FIG. 2 is a detailed oblique side view of a sample container connecting part 7. In the foreground, the side where a sample container, not shown, for example a syringe, is attached or slid on has two ventilation channels 7.1, which are provided as ventilation slits in the area of the sample container attachment device 7.3. A hollow aspiration tube 7.2 serves for transporting a sample and protrudes into the liquid sample of the sample container. On the side of FIG. 2 facing away, the sample container connecting part is, opposite the aspiration tube 7.2, a Luer taper 7.4 for releasably attaching an analyzer connecting part, not shown in FIG. 2, for example a clot catcher. Snap hooks 7.5 serve for unreleasably connecting the sample container connecting part 7 and the analyzer connecting part.

Figure 3:
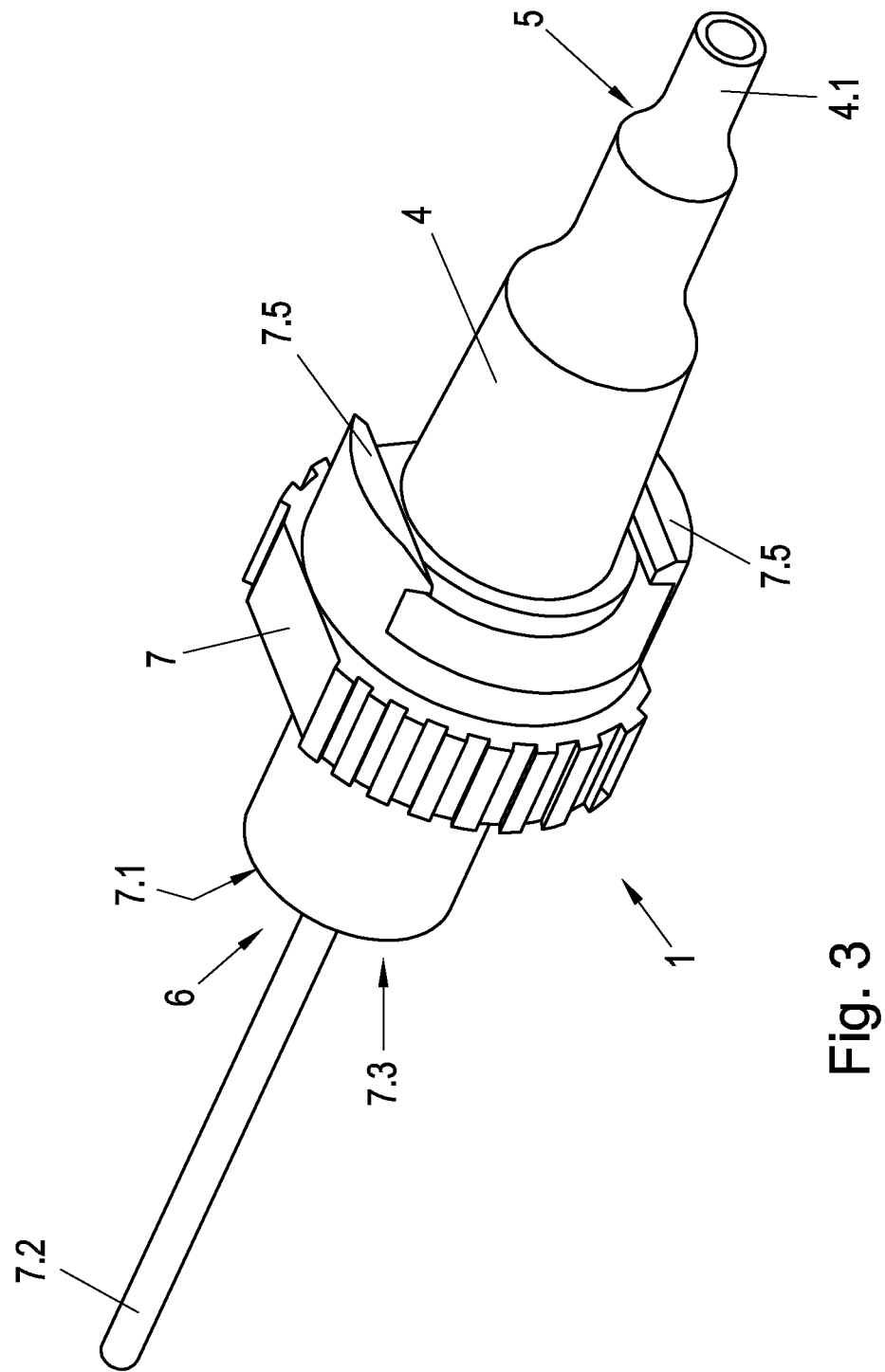
FIG. 3 is an oblique front view of the sample container connecting part shown in FIG. 2 with an analyzer connecting part attached thereto.

FIG. 3 is an oblique front view of the sample container connecting part 7 shown in FIG. 2 with an analyzer connecting part 4 attached thereto. The analyzer connecting part 4 is furthermore provided with an attachment area 4.1 to an analyzer 3 (not shown here). In this case, the retention element 5 (not explicitly shown here, but the spatial position within the analyzer connecting part 4 is indicated by an arrow) is, for example, a mechanical grid that at least partly keeps particulate components of the sample from passing over from the sample container into the analyzer. In addition to the connection between the sample container connecting part 7 and the analyzer connecting part 4 by means of a Luer connection, attachment by snap hooks 7.5 can be used.

Figure 4:
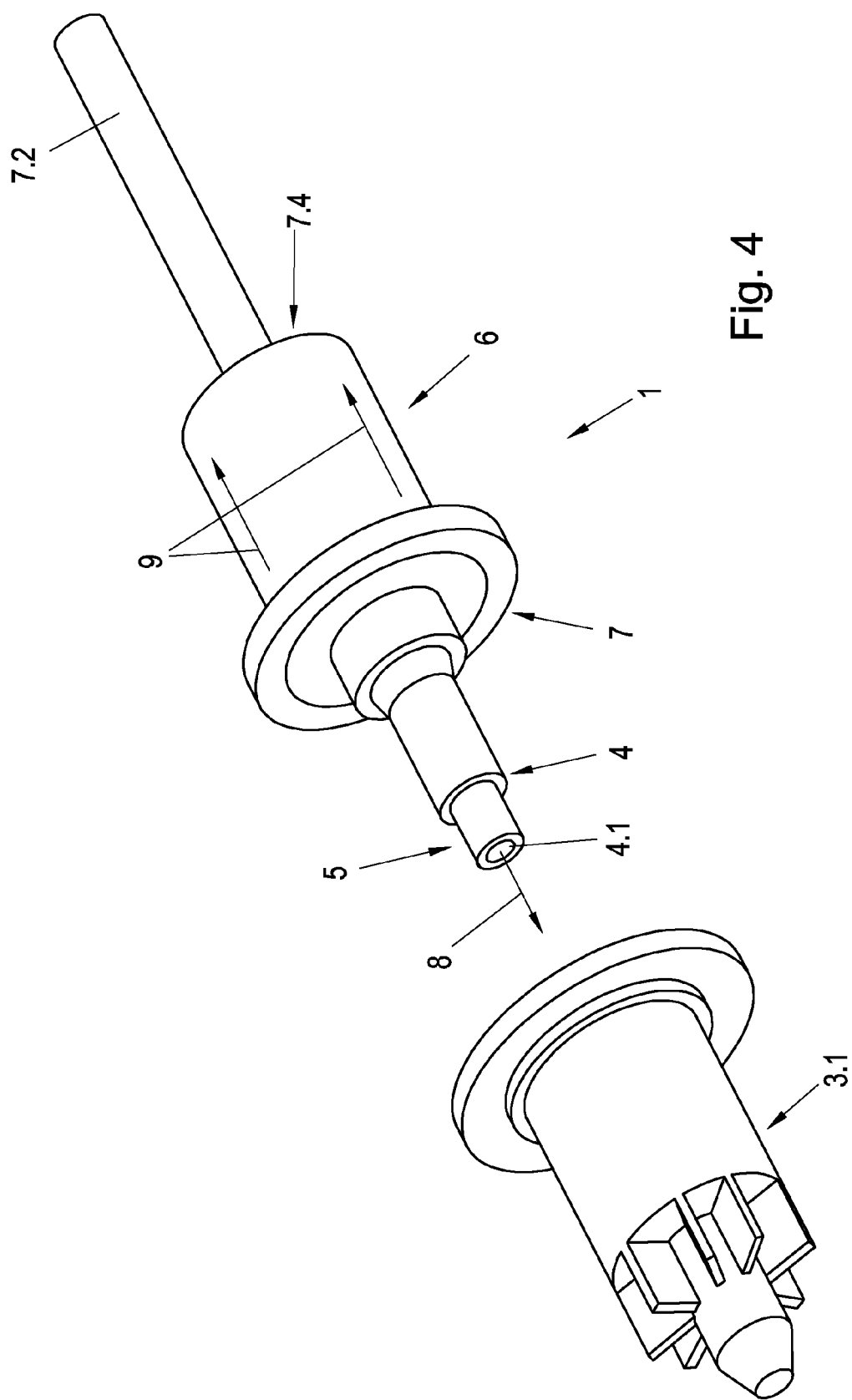
FIG. 4 is an extremely simplified exploded view of a sample input device with the filling mouth of an analyzer.

FIG. 4 is an extremely simplified exploded view of a sample input device 1 with a so-called filling mouth 3.1, which constitutes the sample entrance of an analyzer (not shown).

In this case, the analyzer connecting part 4 and the sample container connecting part 7 of the sample input device 1 are shown in connected positions. The analyzer connecting part 4 comprises several retention elements 5, the sample container connecting device 7 is provided with ventilation devices 6. The free end of the analyzer connecting part 4 shown in the foreground has an attachment area 4.1 to an analyzer. The opposite free end of the sample input device 1 shown in the background of the drawing, to which a sample container may be connected, is provided with an aspiration tube 7.2 as well as a Luer taper 7.4 for releasable connection with a sample container.

Figure 5:
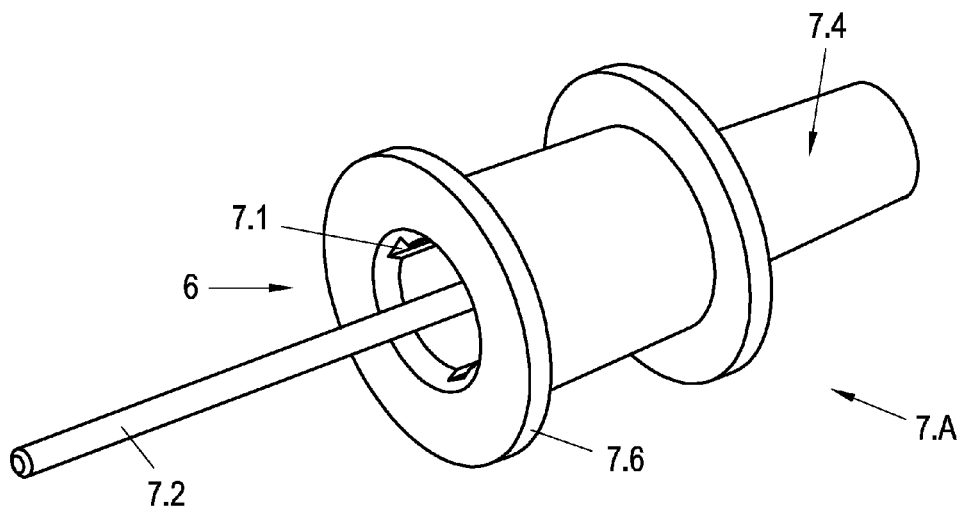
FIG. 5 is a detailed oblique side view of a further embodiment of a sample container connecting part.

FIG. 5 is a detailed oblique side view of a further embodiment of a sample container connecting part 7.A. Here, an additional circumferential ring 7.6 is provided for improved haptic features and to allow use with Luer lock syringes.

Figure 6:
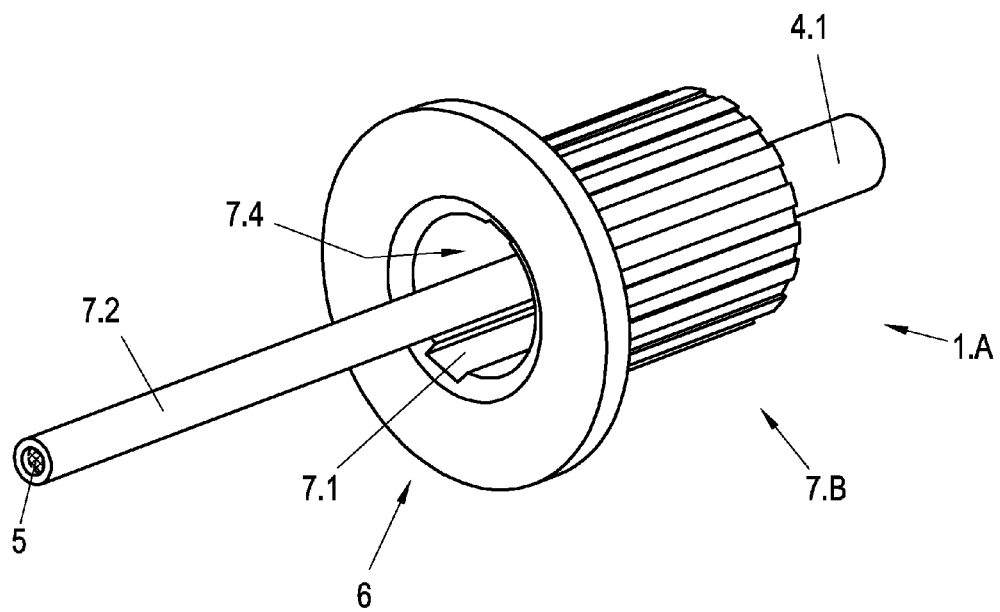
FIG. 6 is an oblique view of a further embodiment of a single-piece sample input device.

FIG. 6 is an oblique view of a further embodiment of a single-piece sample input device 1.A. Here, the sample container connecting part 7.B has an aspiration tube 7.2 on the free end thereof, which is provided with a retention element 5 in the interior. Thus, in addition to ventilating, the sample container connecting part 7.B also functions as a clot catcher. The free end of the single-piece sample input device 1.A opposite the aspiration tube 7.2 may thus be directly attached at the analyzer connecting part 4.1 thereof to an analyzer (not shown). No separate analyzer connecting part, for example a known clot catcher, is necessary in this case.

Of course it is also possible within the framework of an embodiment of the disclosure to combine the sample input device 1.A with an analyzer connecting part and thus provide a sample input device with several retention elements spaced apart.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A sample input device for transferring a liquid sample from a sample container into an analyzer for examining the composition of the liquid sample, wherein the sample input device comprises:
   at least one retention element that at least partly keeps particulate components of the liquid sample from passing over from the sample container into the analyzer while transferring the liquid sample from the sample container into the analyzer, and
   at least one ventilation device that allows ventilating the sample container while transferring the liquid sample from the sample container into the analyzer,
   wherein the at least one retention element and the at least one ventilation device are implemented in individual components, wherein the individual components are assembled together in a tight manner by a Luer taper connection to provide a functional unit, and
   wherein one of the individual components comprises an analyzer connecting part, which is connectable to a sample entrance of the analyzer.

2. The sample input device of claim 1, wherein the at least one ventilation device allows ventilating the sample container when aspirating the sample via the analyzer.

3. The sample input device of claim 1, wherein the liquid sample is blood.

4. The sample input device of claim 1, wherein the sample container is a syringe.

5. The sample input device of claim 1, wherein the at least one retention element is provided as a mechanical retention device.

6. The sample input device of claim 5, wherein said mechanical retention device is a grid, filter or sieve.

7. The sample input device of claim 1, wherein the at least one ventilation device is provided as a ventilation channel.

8. The sample input device of claim 1, wherein another one of the individual components comprises a sample container connecting part, wherein the sample container connecting part comprises an aspiration tube, and wherein the aspiration tube is insertable into the sample container.

9. The sample input device of claim 8, wherein the at least one retention element is provided in the aspiration tube.

10. The sample input device of claim 1, wherein another one of the individual components comprises a sample container connecting part which is connectable to the sample container.

11. The sample input device of claim 10, wherein the sample container connecting part is made of a material selected from methyl-methacrylate-acrylonitrile-butadien-styrene (MABS), copolyesters, or polyethylene terephthalate.

12. The sample input device of claim 10, wherein the sample container connecting part is made of styrene acrylonitrile (SAN).

13. The sample input device of claim 10, wherein the analyzer connecting part is made of a styrene-ethylene-butylene-styrene material.

14. The sample input device of claim 1, wherein the individual components are unreleasably connected to each other.

15. The sample input device of claim 14 further comprising snap hook connections configured to unreleasably connect said individual components to each other.

16. The sample input device of claim 1, wherein the at least one retention element is arranged in the analyzer connecting part.

17. The sample input device of claim 1, wherein another one of the individual components comprise a sample container connecting part connectable to a sample exit of the sample container, and wherein the at least one ventilation device is provided in the sample container connecting part.

18. The sample input device of claim 1 further comprising a sample container attachment device configured to provide a releasable connection with the sample container.

19. The sample input device of claim 18, wherein the sample container attachment device is a Luer taper connection.

20. The sample input device of claim 18, wherein the at least one ventilation device is provided as ventilation slits in the sample container attachment device.

21. The sample input device of claim 1 further comprising at least one circumferential ring.

22. A method for transferring liquid samples from a sample container into an analyzer for examining the composition of the samples, comprising:
providing a sample input device according to claim 1;
connecting the sample input device to a sample exit of the sample container;
connecting the sample input device to a sample entrance of the analyzer; and
aspirating the liquid sample from the sample container into the analyzer by subpressure created in the analyzer.

23. The sample input device of claim 1, wherein the individual components are only a pair of individual components, wherein another one of the individual components comprises a sample container connecting part.

24. The sample input device of claim 23, wherein the sample container connecting part comprises a sample container attachment device, and the at least one ventilation device is provided as ventilation slits in the sample container attachment device, and the at least one retention element is provided to at least one of the analyzer connecting part and the sample container connecting part.

* * * * *